(12) United States Patent
Sargent

(10) Patent No.: US 6,428,496 B1
(45) Date of Patent: Aug. 6, 2002

(54) BACK TRACTION AID

(76) Inventor: John R. Sargent, 810 Dove Pond Rd., Templeton, CA (US) 93465

( * ) Notice: Subject to any disclaimer, the term of this patent is extended or adjusted under 35 U.S.C. 154(b) by 0 days.

(21) Appl. No.: 09/841,016

(22) Filed: Apr. 24, 2001

(51) Int. Cl.[7] .................................................. A61F 5/00
(52) U.S. Cl. ............................ 602/32; 602/38; 606/241
(58) Field of Search ........................ 602/32–38, 39–40; 482/35, 36, 23, 66, 28, 91, 907; 606/240–242, 237; 135/67–69, 75

(56) References Cited

U.S. PATENT DOCUMENTS

| | | |
|---|---|---|
| 1,374,115 A | 4/1921 | Roemer |
| 1,642,158 A | 9/1927 | Kubista |
| 4,102,336 A | 7/1978 | Wiener et al. |
| 4,282,868 A | 8/1981 | Riggs |
| 4,890,606 A | 1/1990 | Iams et al. |
| 5,038,758 A | 8/1991 | Iams et al. |
| 5,282,834 A | 2/1994 | Remy |
| 5,542,898 A | 8/1996 | Wilkinson |
| 5,637,079 A | 6/1997 | Miller |
| 5,842,960 A * | 12/1998 | Yu .............................. 482/131 |
| 5,983,911 A * | 11/1999 | Steele .......................... 135/66 |
| 6,007,507 A | 12/1999 | Ledany |
| 6,244,285 B1 * | 6/2001 | Gamache ..................... 135/67 |
| 6,248,048 B1 * | 6/2001 | Zuckerman et al. ........ 482/142 |

* cited by examiner

Primary Examiner—Denise M. Pothier
Assistant Examiner—Quang D. Thanh
(74) Attorney, Agent, or Firm—John V. Stewart

(57) ABSTRACT

A frame with two parallel foot-retention bars (1) and two handles (7) that extend beside the hips of a user lying on a horizontal surface. A user inserts his/her feet between the foot-retention bars, and pushes downward on the handles to stretch the spine. The handles preferably are adjustably extendable to accommodate different user sizes. The foot retention bars push the feet away from the body, producing traction in the spine. Preferably, the foot retention bars are adjustably separable. Preferably, each of the handle assemblies (5–7) is pivotable 180 degrees to a compact storage position within the respective frame portion (3). Optionally, the device can be shipped partially assembled, for completion by the user.

4 Claims, 2 Drawing Sheets

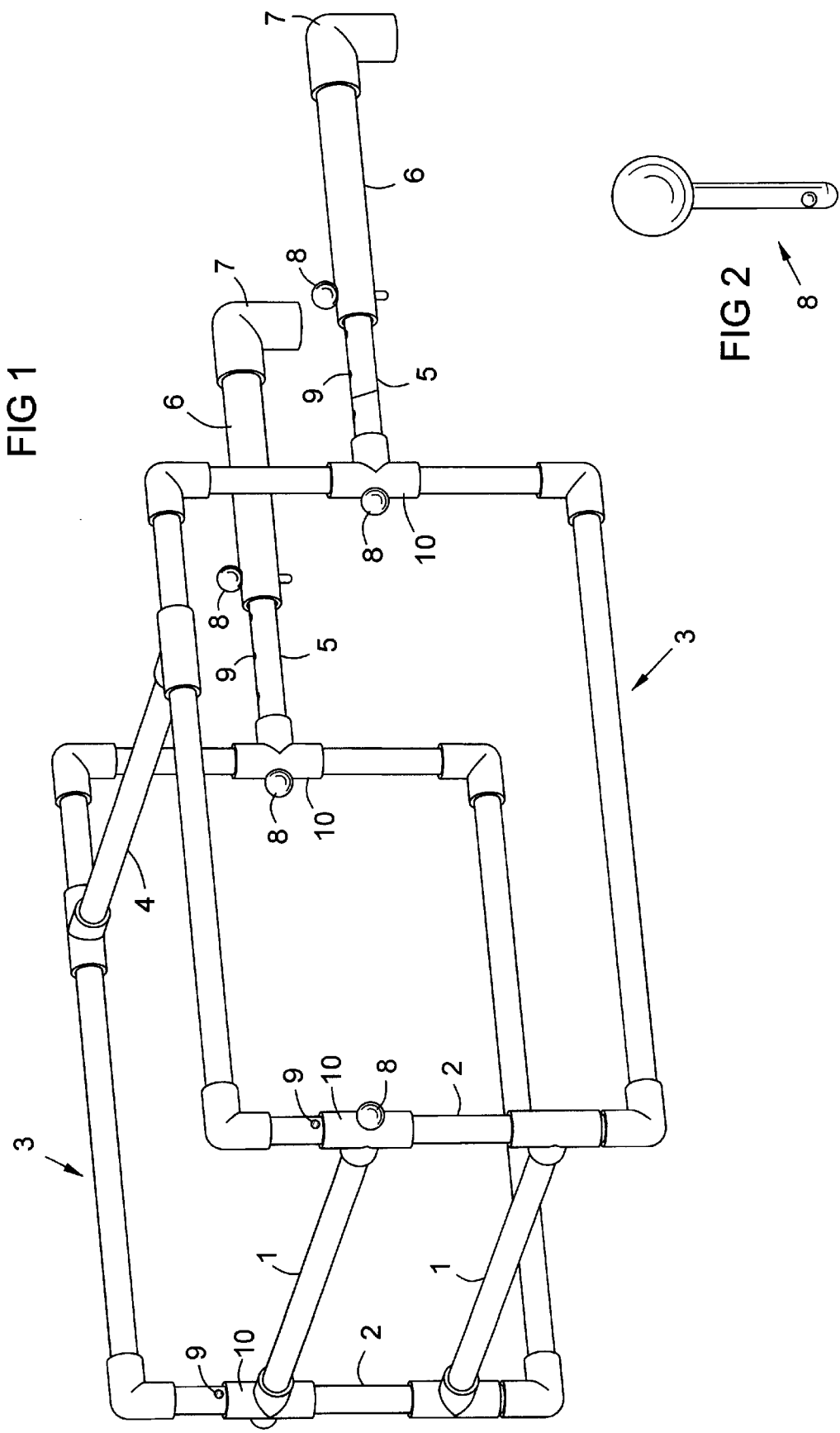

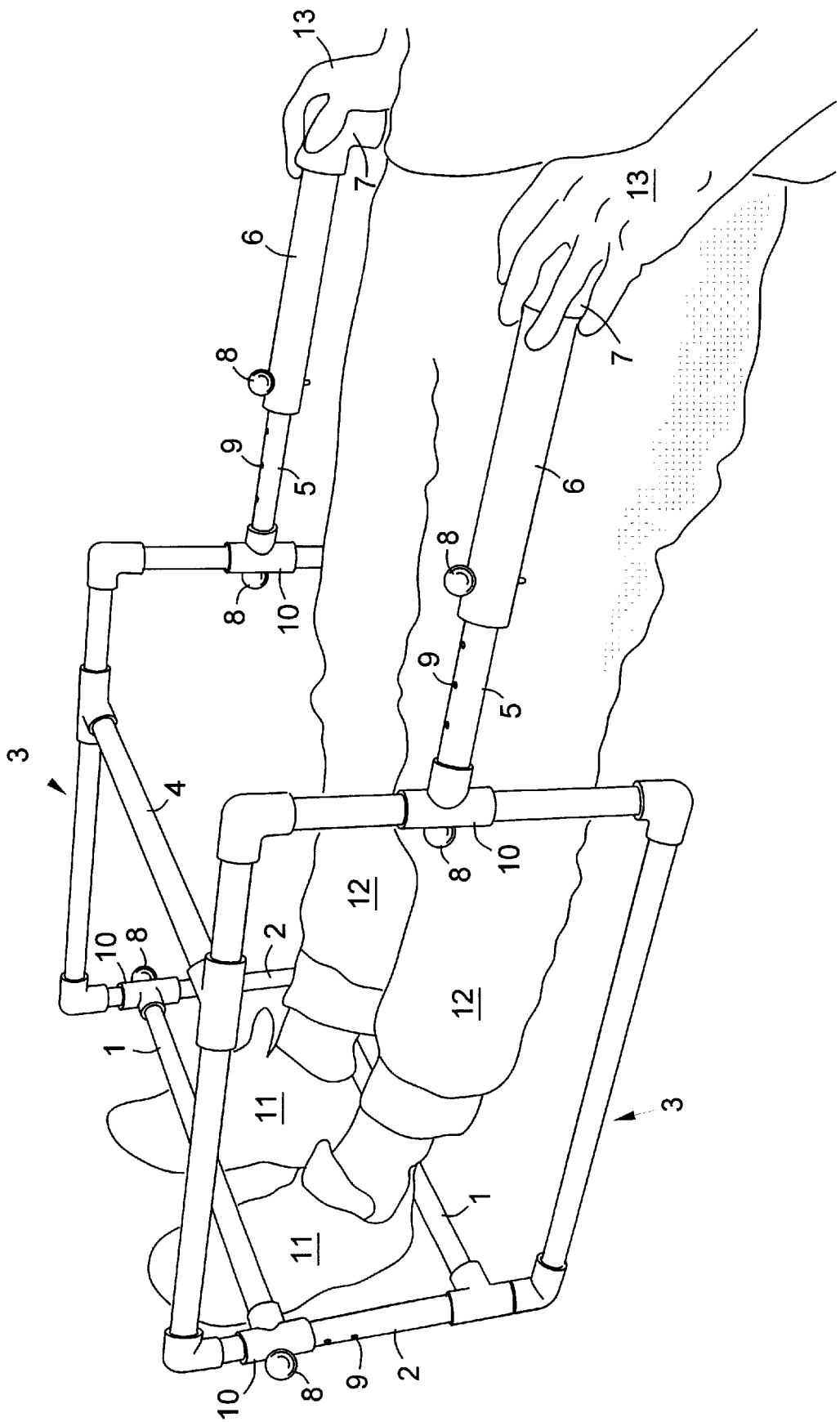

BACK TRACTION AID

BACKGROUND OF THE INVENTION

1. Field of the Invention

This invention relates to devices for applying tensile force, or traction, to the spine of a person.

2. Description of Prior Art

Several types of spinal traction aids have been proposed. Some examples are shown in the following patents:

U.S. Pat. No. 4,102,336 (Weiner 1978)
U.S. Pat. No. 6,007,507 (Ledany 1999)
U.S. Pat. No. 5,282,834 (Remy 1994)
U.S. Pat. No. 1,642,158 (Kubista 1927)
U.S. Pat. No. 4,282,868 (Riggs 1981)
U.S. Pat. No. 1,374,115 (Roemer 1921)
U.S. Pat. No. 5,637,079 (Miller 1997)
U.S. Pat. No. 5,542,898 (Wilkinson 1996)
U.S. Pat. No. 5,038,758 (Iams 1991)
U.S. Pat. No. 4,890,606 (Iams 1990)

However all of the prior devices have one or more of the following disadvantages:

1. Complexity, including moving parts;
2. Inconvenient set-up requirements for each use;
3. Awkward, strained, or ineffective usage;
4. Lack of durability due to inclusion of parts and mechanisms subject to stress concentrations and/or wear, such as bearings that rotate during operation, straps, elastic bands, pads, and rollers;
5. Storage problems due to size, weight, and/or separable parts; and
6. Unnecessary expense.

SUMMARY OF THE INVENTION

The objectives of the present invention are provision of a back traction aid that is effective and simple, has no moving parts; requires no significant set-up for each use; is comfortable to use; has no parts subject to significant wear; and is small, light, and inexpensive.

These objectives are achieved by providing a frame that includes two parallel foot-retention bars 1 connected to two handles 7 that extend beside the hips of a user reclining on a horizontal surface. The user lies within the frame with his/her feet inserted between and behind the foot-retention bars, and pushes downward on the handles to stretch the spine. The handles preferably have adjustable extension positions to accommodate different sizes of people.

BRIEF DESCRIPTION OF THE DRAWINGS

FIG. 1 is a perspective view of an example of the invention.

FIG. 2 is an enlarged perspective view of an example fixing pin.

FIG. 3 is a perspective view of the invention in operation by a user.

REFERENCE NUMBERS

1. Foot retention bar
2. Cross member
3. Rectangular frame section
4. Rectangular frame section interconnection tube
5. Handle extension inner bar or tube
6. Handle extension outer tube
7. Handle
8. Adjustment fixing pin, bolt, or clip
9. Adjustment hole
10. Slidable T-fifting
11. Foot of a user
12. Leg of a user
13. Hand of a user

DETAILED DESCRIPTION

FIG. 1 shows a frame 3 supporting two parallel foot-retention bars 1 and two handles 7 on extension bar assemblies 5–7. The foot-retention bars admit a user's feet between them when each foot is aligned with the bars. After inserting the feet between the bars, the user turns the feet perpendicular to the bars. The bars then retain the feet against movement of the feet toward the user's body. FIG. 3 shows the retention bars pressing against both of the user's feet, pushing the feet in a direction away from his/her body substantially parallel to his/her legs, creating tensile force in his/her spine to stretch his/her spine.

Preferably the parallel foot-retention bars have adjustable separation, as shown. For example a slidable T-fitting 10 can be provided on each end of the upper foot-retention bar 1. The slidable fitting is fixed in any of two or more positions by a pin 8 inserted through the T-fitting and the respective cross member 2.

FIG. 2 shows a user lying on a horizontal surface, such as a floor or bed. The user's feet are retained by the bars 1, and a handle 7 is beside each hip of the user. The user pushes on the handles 7 toward the feet. This creates compression in the user's arms, in the handles and extension assemblies 5–7, and in the frame sections 3 of the traction aid. This compression results in corresponding opposed traction in the user's legs and spine.

On the first usage by a given user, the handles can be adjusted to a comfortable and effective extension via telescoping extension bars 5–6. Any common type of telescoping tube with adjustable fixing means can be used for this. The example shown is an inner bar or tube 5, and an outer tube 6. The outer tube slides over the inner tube, and is fixed at any of several selectable extensions by a fixing pin 8 inserted through a hole in the outer tube and a selectable one of several holes 9 in the inner tube. The pin can have a knob on one end and a spring-loaded ball partly protruding from a side of the other end. This allows quick adjustment by simply pulling the pin out, sliding the outer tube to a new position where holes in the inner and outer tube are aligned, and pushing the pin through the aligned holes. The spring-loaded ball retains the pin in the holes.

The handle extension bars can preferably rotate approximately 180 degrees using a pivot mechanism such as a slidable T-fitting 10 as shown, to quickly reduce the size of the device for storage or transport. The T-fitting can be fixed in either of two positions 180 degrees apart with a pin 8.

No relative movement occurs between elements in the device during operation. There are no substantial stress concentrations or wearing surfaces. The device can be inexpensively built of steel tubing, aluminum tubing, polyvinyl chloride (PVC) tubing, or other such materials or combinations thereof. For example, a satisfactory working prototype was built of ½" schedule 40 PVC tubing and fittings, which is very inexpensive.

A suggested range of adjustment for the distance of separation between the foot retention bars is approximately 6–10 inches. A suggested range of adjustment for the distance of each handle from the plane of the foot retention bars is approximately 34–42 inches. However the adjustment ranges are at the preference of the product designer for a given market.

Optionally, the device as shown in the drawings can be shipped partially assembled. For example, the rectangular frame sections 3 can be factory assembled with all attached fittings. These rectangular sections can be packaged along with two foot-retention bars 1, an interconnection tube 4, and two handle assemblies 5–7. Each free end of each tube to be attached to the rectangular sections can have a hole through each side. The open end of each T-fitting can have a matching hole through each side. Fasteners such as cotter pins, screws, or quick-release pins as in FIG. 2 can be provided so the user can insert the free ends of the tubes in the respective T-fittings, align the holes, and fix the assembly with the fasteners. This option provides reduced manufacturing cost, very compact shipping, and correspondingly less expense to the user. If quick-release pins are used, the user can quickly disassemble the device for compact storage and transport.

Although the present invention has been described herein with respect to preferred embodiments, it will be understood that the foregoing description is intended to be illustrative, not restrictive. Modifications of the present invention will occur to those skilled in the art. All such modifications that fall within the scope of the appended claims are intended to be within the scope and spirit of the present invention.

I claim:

1. A back traction aid comprising:
   first and second generally parallel foot retention bars in a first plane, each foot retention bar having respective first and second ends;
   a first cross member connected to, and spanning between, the first ends of the foot retention bars;
   a second cross member connected to, and spanning between, the second ends of the foot retention bars;
   a first rectangular frame portion having the first cross member as one of four sides, the first rectangular frame portion lying in a second plane that is approximately perpendicular to the foot retention bars;
   a second rectangular frame portion having the second cross member as one of four sides, the second rectangular frame portion lying in a third plane that is approximately perpendicular to the foot retention bars;
   first and second generally parallel handle extension bars attached to the first and second rectangular frame portions respectively, the parallel handle extension bars lying in first and second lines respectively that are approximately perpendicular to the first plane;
   first and second handles on the respective first and second handle extension bars, the handles fixable on the handle extension bars at an adjustable range of distances from the first plane;
   whereby a user can place the traction aid on a horizontal surface, lie with his/her legs between the rectangular frame portions, insert his/her feet between the foot-retention bars, and manually push the handles toward the feet to stretch the spine.

2. A back traction aid comprising:
   first and second generally parallel foot retention bars for admitting a user's ankles, each retention bar having first and second ends the foot retention bars lying substantially in a first plane;
   a frame attached to the foot retention bars, the frame comprising a first cross member connected to, and spanning between, the first ends of the foot retention bars, a second cross member connected to, and spanning between, the second ends of the foot retention bars, a mechanism on each of the cross members for adjusting the distance of separation between the foot retention bars, a first rectangular portion of the frame having the first cross member as one of four sides, the first rectangular portion lying in a second plane that is approximately perpendicular to the foot retention bars, a second rectangular portion of the frame having the second cross member as one of four sides, the second rectangular portion lying in a third plane that is approximately parallel to the second plane; and
   a left handle and a right handle mounted on the frame in reach of a user's hands approximately beside his/her hips when his/her ankles are between the foot retention bars, the foot retention bars are against his/her feet, and his/her legs are straight the handles mounted at an adjustable range of distances from the foot retention bars;
   whereby a user can place the traction aid on a horizontal surface, lie between the handles with his/her ankles between the foot retention bars, and manually push the handles toward his/her feet, thus pushing the retention bars against his/her feet to stretch his/her spine.

3. The back traction aid of claim 2, wherein first and second handle extension bars are attached to the respective first and second rectangular portions of the frame by respective first and second pivot mechanisms that allow each extension bar to pivot approximately 180 degrees about the respective pivot mechanism for compact storage of the back traction aid, and the left and right handles are attached to the first and second handle extension bars respectively.

4. A back traction method comprising the steps of:
   a) providing first and second generally parallel foot retention bars having an adjustable gap between them for admitting a user's ankles;
   b) providing a frame attached to the foot retention bars;
   c) providing a left handle and a right handle mounted on the frame in reach of a user's hands approximately beside his/her hips when the foot retention bars are against his/her feet and his/her legs are straight;
   d) placing the frame on a horizontal surface; and
   e) a user lying between the handles with his/her ankles between the foot retention bars, and manually pushing the handles toward his/her feet; whereby both of the retention bars press against both of his/her feet pushing the feet in a direction away from his/her body substantially parallel to his/her legs, creating tensile force in his/her spine to stretch his/her spine.

\* \* \* \* \*